United States Patent [19]
Ohno et al.

[11] Patent Number: 5,382,724
[45] Date of Patent: Jan. 17, 1995

[54] PROCESS FOR PURIFYING 1,1,1,2-TETRAFLUOROETHANE

[75] Inventors: Hiromoto Ohno; Tatsuharu Arai; Koichi Katamura; Sadayoshi Yuge; Haruyuki Kawai; Yasuaki Morito, all of Kanagawa, Japan

[73] Assignee: Showa Denko Kabushiki Kaisha, Tokyo, Japan

[21] Appl. No.: 216,780

[22] Filed: Mar. 23, 1994

Related U.S. Application Data

[63] Continuation of Ser. No. 56,783, May 4, 1993, abandoned.

[30] Foreign Application Priority Data

Aug. 20, 1992 [JP] Japan ................... 4-221833

[51] Int. Cl.⁶ .................. C07C 17/38; C07C 19/08
[52] U.S. Cl. ..................... 570/178; 570/177
[58] Field of Search ................... 570/178, 177

[56] References Cited

U.S. PATENT DOCUMENTS

| | | | |
|---|---|---|---|
| 2,478,362 | 8/1949 | Benning | 570/178 |
| 4,911,792 | 3/1990 | Manzer et al. | 570/178 |

FOREIGN PATENT DOCUMENTS

| | | | |
|---|---|---|---|
| 0542290 | 5/1993 | European Pat. Off. | 570/177 |
| 9104955 | 4/1991 | WIPO | 570/177 |

*Primary Examiner*—Alan Siegel
*Attorney, Agent, or Firm*—Sughrue, Mion, Zinn, Macpeak & Seas

[57] ABSTRACT

A process for purifying 1,1,1,2-tetrafluoroethane which comprises allowing an HF-containing 1,1,1,2-tetrafluoroethane-concentrated fraction to contact at a low temperature with hydrofluoric acid which is an extraction solvent and has an HF concentration equal to or higher than an HF concentration at a water-HF azeotropic point, thereby effecting two-phase separation, and subsequently recovering 1,1,1,2-tetrafluoroethane from the separated lower phase, wherein hydrofluoric acid to be used as the extraction solvent has a concentration of from 38 to 70% by weight, and the extraction and two-phase separation steps are effected at a temperature of from −35° to 35° C. According to the purification process, HF can be recovered economically from a 1,1,1,2-tetrafluoroethane fraction containing a small amount of HF.

11 Claims, 1 Drawing Sheet

PROCESS FOR PURIFYING 1,1,1,2-TETRAFLUOROETHANE

This is a continuation of application Ser. No. 08/056,783 filed May 4, 1993, now abandoned.

FIELD OF THE INVENTION

This invention relates to a process for the purification of 1,1,1,2-tetrafluoroethane (referred to as "$CF_3-CH_2F$" or "HFC-134a" hereinafter) in which HF is removed for reuse from an HF-containing HFC-134a concentrate which has been obtained by distillation treatment of reaction products formed in a process for the production of HFC-134a by the reaction of trichloroethylene (referred to as "$CCl_2=CHCl$" or "trichlene" hereinafter) and HF.

BACKGROUND OF THE INVENTION

In general, when HFC-134a is produced from trichlene and HF as starting materials, the production process is effected by two reaction steps. That is, trichlene is allowed to react with HF as a first step reaction based on the following formula (1) to form 1,1,1-trifluoro-2-chloroethane (referred to as "$CF_3-CH_2Cl$" or "HCFC-133a" hereinafter), and then the thus formed HCFC-133a is allowed to react with HF based on the following formula (2) as a second step reaction to obtain HFC-134a.

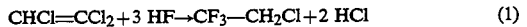

$CHCl=CCl_2 + 3\ HF \rightarrow CF_3-CH_2Cl + 2\ HCl$ (1)

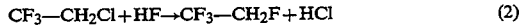

$CF_3-CH_2Cl + HF \rightarrow CF_3-CH_2F + HCl$ (2)

Each of these reactions is carried out in the presence of an alumina-chromina catalyst, but under different reaction conditions: the first step reaction being effected under a pressure of 4 kg/cm$^2$G, at a temperature of 250° C. and with an HF/trichlene mol ratio of 6/1; and the second step reaction is carried out under a pressure of 4 kg/cm$^2$G, at a temperature of 350° C. and with an HF/HCFC-133a mol ratio of 4/1. The thus formed reaction products are separated by distillation which may be effected by various distillation systems. In any of the distillation systems, HCl is recovered as a by-product to be used for other purposes, and HF and HCFC-133a are recycled as reaction materials. HFC-134a as the product of interest is concentrated by the distillation and separated as a fraction containing small amounts of HCFC-133a and HF.

The presence of small amounts of HCFC-133a and HF in the HFC-134a fraction is attributable to the minimum azeotropic points of HCFC-133a with HF and HFC-134a with HF. That is, in the second step reaction under a pressure of 4 kg/cm$^2$G, the former mixture has an azeotropic point of 41° C. at which its HCFC-133a/HF compositional ratio becomes 62 mol %/38 mol %, and the latter mixture has an azeotropic point of 14° C. at which its HFC-134a/HF compositional ratio becomes 87 mol %/13 mol %.

Since HCFC-133a or HF cannot be removed from HFC-134a by distillation alone because of the above reason, HF is removed generally by way of alkali washing. Once HF is removed, HCFC-133a and other fluorocarbons can be separated from HFC-134a by distillation because they have no azeotropic relation with HFC-134a.

As described above, removal of HF from a concentrated HFC-134a fraction has been effected by alkali washing in the prior art. However, such a washing step not only requires an alkali agent but also entails discharge of the expensive HF and further causes a disadvantage because of the requirement of waste water treatment.

SUMMARY OF THE INVENTION

An object of the present invention is to provide a process for the purification of 1,1,1,2-tetrafluoroethane (HFC-134a) by which HF can be recovered economically from a concentrated HFC-134a fraction containing small amounts of 1,1,1-trifluoro-2-chloroethane (HCFC-133a) and HF.

The present invention is a process for purifying HFC-134a from an HF-containing HFC-134a fraction obtained by allowing trichloroethylene to react with HF and be concentrated through a distillation step, which comprises allowing the HF-containing HFC-134a-concentrated fraction to contact at a low temperature with hydrofluoric acid which is an extraction solvent and has an HF concentration equal to or higher than an HF concentration at a water-HF azeotropic point, thereby effecting two-phase separation, and subsequently recovering HFC-134a from the lower phase.

Preferably, hydrofluoric acid to be used as the extraction solvent has a concentration of from 38 to 70% by weight, and the extraction and two-phase separation steps are effected at a temperature of from −35° to 35° C.

DETAILED DESCRIPTION OF THE INVENTION

The gist of the present invention resides in that a concentrated HFC-134a fraction containing small amounts of HCFC-133a and HF is brought into contact at a low temperature with hydrofluoric acid which is an extraction solvent and has an HF concentration equal to or higher than an HF concentration at a water-HF azeotropic point, effecting two-phase separation and the HFC-134a is subsequently recovered from the separated lower phase, thereby enabling economical separation of HF. The thus separated HF can be re-used as such.

The process of the present invention is explained in detail with reference to FIG. 1.

Figure 1:
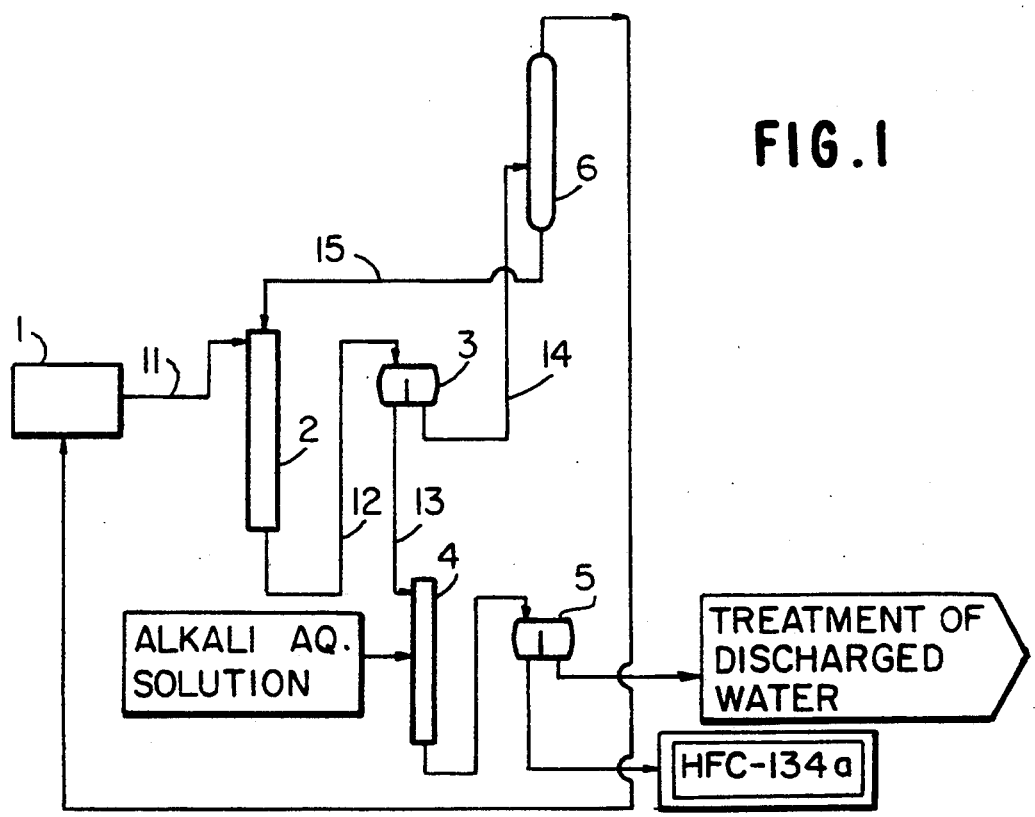
FIG. 1 is a flow diagram showing an example of the process of the present invention.

In FIG. 1, 1 is a reaction system, 2 is an extraction column, 3 is a first decanter, 4 is a washing column, 5 is a second decanter, 6 is an HF recovering column, 11 is a concentrated HFC-134a fraction, 12 is a bottom liquid discharged from the extraction column, 13 is a liquid discharged from the lower layer in the first decanter, 14 is hydrofluoric acid discharged from the upper layer in the first decanter, and 15 is an extraction solvent.

FIG. 1 is a flow diagram showing an example of the HFC-134a purification process of the present invention in which the reference number 1 is a reaction system that comprises reactors and distillation columns. The reaction system 1 may be selected from various process flow systems, but a concentrated HFC-134a fraction discharged therefrom may contain small amounts of HF, HCFC-133a and the like and have almost the same composition independent of the reaction system employed. The concentrated HFC-134a fraction 11 is introduced into an extraction column 2.

The concentrated HFC-134a fraction to be purified in the present invention generally has an HFC-134a concentration of at least 80% by weight, preferably 90% by weight or more, an HF content of less than 5% by weight, preferably less than 2.5% by weight, and an HCFC-133a content of less than 20% by weight, preferably 10% by weight.

Into extraction column 2 is introduced hydrofluoric acid (a bottom liquid from HF recovering column 6, which will be described later) as extraction solvent 15 which has an HF concentration equal to or higher than its concentration (38% by weight) at an azeotropic point of an HF/water system that has a maximum azeotropic point of 112.4° C. at which its $HF/H_2O$ compositional ratio becomes 35.8 mol %/64.2 mol %. The resulting mixture is kept at a low temperature to effect extraction.

After completion of the extraction, liquid 12 discharged from the bottom of extraction column 2 is introduced into first decanter 3 where two-phase separation is effected, and liquid 13 discharged from the lower layer is introduced into washing column 4 to remove remaining small amounts of HF and HCl by alkali washing using, e.g., a weakly alkaline aqueous solution. A bottom liquid from washing column 4 is introduced into second decanter 5 where two-phase separation is effected, and HFC-134a in the resulting lower layer is recovered and the upper water layer is introduced into a waste water treatment system.

Hydrofluoric acid 14 having increased HF concentration from the upper layer of first decanter 3 is introduced into HF recovering column 6 where HF is separated by distillation. The thus recovered HF is recycled into reaction system 1. The bottom liquid discharged from HF recovering column 6 is a hydrofluoric acid fraction containing HF at a concentration equal to or higher than the HF/water azeotropic concentration, which is used as extraction solvent 15 in extraction column 2.

Small amounts of HCFC-133a and other fluorocarbons originally contained in concentrated HFC-134a fraction 11 are finally contained in the lower layer of second decanter 5. Since these trace components have no azeotropic relation in the absence of HF, they can be separated and purified by a subsequent distillation step.

In the purification process of the present invention, HF concentration of hydrofluoric acid (bottom liquid in HF recovering column 6) to be used as extraction solvent 15 is dependent upon the distillation/separation capacity of HF recovering column 6 and the HF concentration of hydrofluoric acid 14 to be introduced into the column from the upper layer of first decanter 3, but lower limit of the HF concentration of hydrofluoric acid to be used as extraction solvent 15 becomes a value equal to or higher than the HF concentration (38% by weight) at the maximum water/HF azeotropic point as long as HF is recovered by the distillation separation.

Since liquid density of hydrofluoric acid increases with increase in the HF concentration, difference in the density between hydrofluoric acid and HFC-134a becomes very small when HF concentration of extraction solvent 15 exceeds 70% by weight under an operation temperature condition which will be described later, thus causing difficulty in effecting two-phase separation in first decanter 3. In consequence, HF concentration of hydrofluoric acid to be used as extraction solvent 15 in extraction column 2 may be controlled within the range of preferably from 38 to 70% by weight, more preferably from 45 to 55% by weight.

Operation temperatures in extraction column 2 and first decanter 3 may be controlled within the range of preferably from −35° to 35° C., more preferably from 5° to 25° C. Lower limit of the operation temperature is restricted by the solidification point of hydrofluoric acid under an operation pressure and at an HF concentration at the time of the operation, or by the forming temperature of HFC-134a hydrate. Operation at a temperature lower than the lower limit therefore will cause problems in the process lines, such as blockage and the like. In addition, since hydrofluoric acid and HFC-134a have different tendencies in terms of temperature-dependent changes in the liquid density, their liquid densities become close as the liquid temperature increases and are finally reversed. Because of this, two-phase separation in first decanter 3 cannot be effected when the operation temperature exceeds the just described upper limit.

Figure 2:
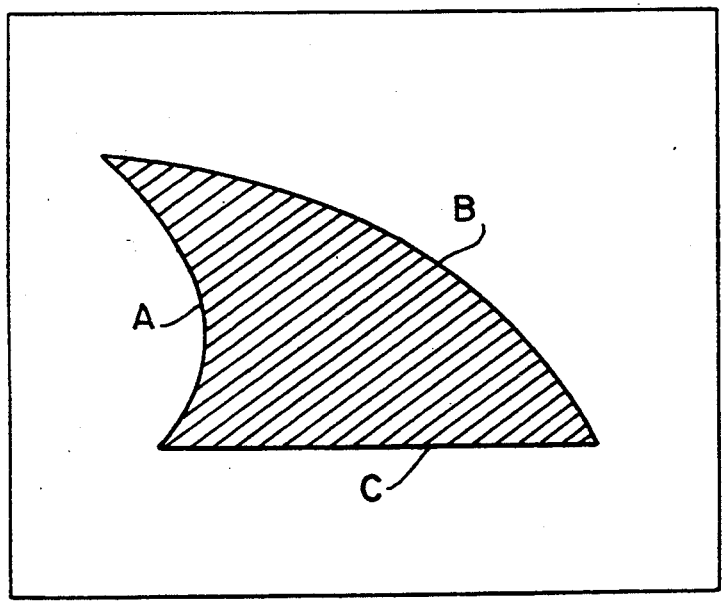
FIG. 2 is a conceptual view showing ranges of operation conditions in the practice of the process of the present invention.

As has been described above, the HF concentration of extraction solvent 15 and the extraction/separation temperature selectable in the purification process of the present invention have a mutual relation. A conceptual view in relation to the ranges of the operation conditions in the practice of the process of the present invention is shown in FIG. 2. In this figure, the line A is a borderline defined by solidification points of a hydrofluoric acid aqueous solution at respective HF concentrations or by formation temperatures of HFC-134a hydrates. The line B is a borderline defined by temperature-dependent changes in the density of hydrofluoric acid aqueous solution, in order to prevent inversion between the densities of HFC-134a and hydrofluoric acid in first decanter 3. The line C is a borderline defined by the HF azeotropic concentration in hydrofluoric acid aqueous solution. As the operation conditions, optional combinations of interface controllable conditions may be selected within the area surrounded by the lines A, B and C as shown in FIG. 2.

Though not particularly limited, the operation may be carried out under a pressure of preferably 10 kg/cm$^2$G or below taking pressure resistance and the like of process equipments into consideration, more preferably within the range of from 6 to 7 kg/cm$^2$G taking the process workability and profitability into consideration. The operation pressure if higher than 10 kg/cm$^2$G would require special equipments for high pressure use, and if lower than 6 kg/cm$^2$G would require a special means in order to prevent volatilization of HFC-134a, thus narrowing selectable ranges of the operation conditions.

EXAMPLES

The following examples are provided to further illustrate the process of the present invention. It is to be understood, however, that the examples are for purpose of illustration only and are not intended to limit the present invention.

Extraction experiments of HFC-134a from the reaction system 1 were carried out making use of the equipments and process steps as shown in FIG. 1, with the results shown in Table 1. In the table, components in each process step in the vicinity of extraction column 2 are indicated by weight percent, and the flow rate in each step is shown as a relative value in which the flow rate of concentrated HFC-134a fraction 11 is taken as 100.

TABLE 1

| Component | 11 | 12 | 13 | 14 | 15 |
|---|---|---|---|---|---|
| [Flow Rate]*1: | | | | | |
| HFC-134a | 88.3 | 68.3 | 88.2 | 0.1 | — |
| HCFC-133a | 6.7 | 6.65 | 6.5 | — | — |
| HF | 1.5 | 4.48 | 0.09 | 4.4 | 2.99 |
| HCl | 0.52 | 0.52 | — | 0.52 | — |
| H$_2$O | — | 4.48 | — | 4.48 | 4.48 |
| Others | 2.98 | 4.43 | 5.21 | 9.9 | — |
| Total | 100 | 107.4 | 98.0 | 19.5 | 7.47 |
| [Weight Ratio]*2: | | | | | |
| HFC-134a | 88.3 | 82.2 | 90.0 | 1.04 | — |
| HCFC-133a | 6.7 | 6.2 | 6.79 | — | — |
| HF | 1.5 | 4.2 | 0.09 | 46.3 | 40 |
| HCl | 0.52 | 0.48 | — | 5.43 | — |
| H$_2$O | — | 4.17 | — | 47.23 | 60 |
| Others | 2.98 | 2.5 | 3.12 | — | — |
| Total | 100 | 100 | 100 | 100 | 100 |

[Note]
*1Flow rate of each component when the flow rate of concentrated HFC-134a fraction 11 is taked as 100 kg/hr.
*2% by weight As is evident from the results shown in Table 1, the greater portion of HF contained in concentrated HFC-134a fraction 11 can be recovered and recycled, by carrying out the extraction/separation operation using extraction solvent 15 which contains HF in an amount higher than the azeotropic HF concentration.

As has been described in the foregoing, the HFC-134a purification process of the present invention is possessed of an advantage in that HF which is contained in an HFC-134a fraction and not separable by distillation can be recycled efficiently by allowing the HF fraction to contact with hydrofluoric acid as an extraction solvent containing HF in an amount equal to or higher than an HF concentration at the water/HF azeotropic point and subsequently effecting two-phase separation. Separation and recovery of HF can be effected more smoothly by setting the concentration of hydrofluoric acid to be used as an extraction solvent to 38 to 70% by weight, and the operation temperature at the time of extraction/separation to −35° to 35° C.

While the invention has been described in detail and with reference to specific embodiments thereof, it will be apparent to one skilled in the art that various changes and modifications can be made therein without departing from the spirit and scope thereof.

What is claimed is:

1. A process for purifying 1,1,1,2-tetrafluoroethane from an HF-containing 1,1,1,2-tetrafluoroethane-concentrated fraction obtained by reacting trichloroethylene with HF and concentrating a resulting reaction product through a distillation step, the process comprising the step of extracting HF from the HF-containing 1,1,1,2-tetrafluoroethane-concentrated fraction by contacting the HF-containing 1,1,1,2-tetrafluoroethane-concentrated fraction at a low temperature with an extraction solvent comprising hydrofluoric acid to extract the HF of the fraction into the extraction solvent, the extraction solvent having an HF concentration equal to or higher than an HF concentration at a water-HF azeotropic point, and subsequently recovering 1,1,1,2-tetrafluoroethane.

2. The purification process according to claim 1, wherein the extraction solvent has a hydrofluoric acid concentration of from 38 to 70% by weight.

3. The purification process according to claim 2, wherein the extraction solvent has a hydrofluoric acid concentration of from 45 to 55% by weight.

4. The purification process according to claim 1, further comprising the steps of recovering a liquid from the extraction step and separating the liquid by two-phase separation into a lower layer and an upper layer.

5. The purification processing according to claim 4, further comprising the steps of distilling the upper layer from the two-phase separation to obtain an HF distillate, and recycling the HF distillate as a starting material for reaction with trichloroethylene.

6. The purification process according to claim 4, wherein the two-phase separation is carried out at −35° to 35° C.

7. The purification process according to claim 6, wherein the two-phase separation is carried out at 5° to 25° C.

8. The purification process according to claim 5, further comprising the step of recovering a liquid from the distilling step and recycling the liquid to the extraction step for use as the extraction solvent.

9. The purification process according to claim 1, wherein the step of contacting the HF-containing 1,1,1,2-tetrafluoroethane-concentrated fraction with an extraction solvent is carried out at a temperature of from −35° to 35° C.

10. The purification process according to claim 9, wherein the step of contacting the HF-containing 1,1,1,2-tetrafluoroethane-concentrated fraction with an extraction solvent is carried out at a temperature of from 5° to 25° C.

11. The purification process according to claim 1, wherein the extraction solvent has a hydrofluoric acid concentration of up to 70% by weight.

* * * * *